US009012454B2

(12) United States Patent
Brozovich

(10) Patent No.: US 9,012,454 B2
(45) Date of Patent: Apr. 21, 2015

(54) SEXUAL DYSFUNCTION

(75) Inventor: Frank V. Brozovich, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 2061 days.

(21) Appl. No.: 12/096,718

(22) PCT Filed: Dec. 8, 2006

(86) PCT No.: PCT/US2006/047044
§ 371 (c)(1),
(2), (4) Date: Jan. 22, 2010

(87) PCT Pub. No.: WO2007/070426
PCT Pub. Date: Jun. 21, 2007

(65) Prior Publication Data
US 2012/0134887 A1 May 31, 2012

Related U.S. Application Data

(60) Provisional application No. 60/749,182, filed on Dec. 9, 2005.

(51) Int. Cl.
*A61K 31/519* (2006.01)
*A61K 31/495* (2006.01)
*A61K 31/53* (2006.01)
*A61K 31/40* (2006.01)
*A61K 31/407* (2006.01)
*A61K 31/4178* (2006.01)
*A61K 31/41* (2006.01)
*A61K 31/4184* (2006.01)
*A61K 31/4985* (2006.01)
*A61K 45/06* (2006.01)

(52) U.S. Cl.
CPC ........... *A61K 31/4178* (2013.01); *A61K 31/495* (2013.01); *A61K 31/40* (2013.01); *A61K 31/407* (2013.01); *A61K 31/41* (2013.01); *A61K 31/4184* (2013.01); *A61K 31/4985* (2013.01); *A61K 31/519* (2013.01); *A61K 31/53* (2013.01); *A61K 45/06* (2013.01)

(58) Field of Classification Search
CPC ... A61K 31/519; A61K 31/495; A61K 31/53; A61K 31/40; A61K 31/407
USPC ................. 514/252.16, 243, 250, 423, 421
See application file for complete search history.

(56) References Cited

U.S. PATENT DOCUMENTS

2004/0063719 A1  4/2004  Adams et al.
2006/0189603 A1  8/2006  Garvey et al.

FOREIGN PATENT DOCUMENTS

| WO | WO 99/12110    | 3/1999  |
| WO | WO 00/12110    | 3/2000  |
| WO | WO 02/24698    | 3/2002  |
| WO | WO 03/020724   | 3/2003  |
| WO | WO 03/042216   | 5/2003  |
| WO | WO 03/101991   | 12/2003 |
| WO | WO 2004/110368 | 12/2004 |
| WO | WO 2006/055542 | 5/2006  |
| WO | WO 2006/104870 | 10/2006 |
| WO | WO 2007/016361 | 2/2007  |

OTHER PUBLICATIONS

Abassi et al., "Impaired nitric oxide-mediated renal vasodilation in rats with experimental heart failure: role of angiotensin II," *Circulation*, 1997, 96(10):3655-3664.
Awan et al., "Efficacy of ambulatory systemic vasodilator therapy with oral prazosin in chronic refractory heart failure. Concomitant relief of pulmonary congestion and elevation of pump output demonstrated by improvements in symptomatology, exercise tolerance, hemodynamics and echocardiography," *Circulation*, 1977, 56(3):346-354.
Carson et al., "Racial differences in response to therapy for heart failure: analysis of the vasodilator-heart failure trials," *J. Card. Fail.*, 1999, 5(3):178-187.
Cohn et al., "Effect of vasodilator therapy on mortality in chronic congestive heart failure. Results of a Veterans Administration Cooperative Study," *N. Engl. J. Med.*, 1986, 314:1547-1552.
Delp et al., "Changes in skeletal muscle biochemistry and histology relative to fiber type in rats with heart failure," *J. Appl. Physiol.*, 1997, 83(4):1291-1299.
Deswal et al., "Cytokines and cytokine receptors in advanced heart failure. An analysis of the cytokine database from the Vesnarinone trial (VEST)," *Circulation*, 2001, 103:2055-2059.
Dirksen et al., "A myosin phosphatase targeting subunit isoform transition defines a smooth muscle developmental phenotypic switch," *Am. J. Physiol. Cell Physiol.*, 2000, 278:C589-C600.
Dzau, "Tissue angiotensin and pathobiology of vascular disease. A unifying hypothesis," *Hypertension*, 2001, 37:1047-1052.
Furchgott, "Endothelium-derived relaxing factor: discovery, early studies, and identification as nitric oxide," *Biosci. Rep.*, 1999, 19(4):235-251.
Griendling et al., "Angiotensin II stimulates NADH and NADPH oxidase activity in cultured vascular smooth muscle cells," *Circ. Res.*, 1994, 74:1141-1148.
Hartshorne et al., "Myosin light chain phosphatase: subunit composition, interactions and regulation," *J. Muscle Res. Cell Motil.*, 1998, 19:325-341.
Huang et al., "Unzipping the role of myosin light chain phosphatase in smooth muscle cell relaxation," *J. Biol. Chem.*, 2004, 279:597-603.
Hunter et al., "Tumor necrosis factor-α-induced activation of RhoA in airway smooth muscle cells: role in the $Ca^{2+}$ sensitization of myosin light $chain_{20}$ phosphorylation," *Mol. Pharmacol.*, 2003, 63:714-721.

(Continued)

*Primary Examiner* — Raymond Henley, III
(74) *Attorney, Agent, or Firm* — Fish & Richardson P.C.

(57) ABSTRACT

This document provides methods and materials related to treating mammals (e.g., humans) having a sexual dysfunction that is refractory to treatment with a PDE V inhibitor. For example, methods and materials related to the use of an ACE inhibitor and/or an angiotensin II receptor blocker with a PDE V inhibitor to treat mammals having a sexual dysfunction (e.g., erective dysfunction) that is unresponsive to treatment with a PDE V inhibitor are provided.

29 Claims, 3 Drawing Sheets

(56) References Cited

OTHER PUBLICATIONS

Isabelle et al., "Role of $\alpha_1$-adrenoreceptors in cocaine-induced NADPH oxidase expression and cardiac dysfunction," *Cardiovasc. Res.*, 2005, 67:699-704.

Jessup and Brozena, "Heart failure," *N. Engl. J. Med.*, 2003, 348:2007-2018.

Johnson and Lincoln, "Effects of nitroprusside, glyceryl trinitrate, and 8-bromo cyclic GMP on phosphorylase $\alpha$ formation and myosin light chain phosphorylation in rat aorta," *Mol. Pharmacol.*, 1985, 27:333-342.

Johnson, "Tablets and Capsules" Sustained Release Medications, Chemical Technology Review No. 177, Park Ridge, Noyes Data Corporation, 1980, pp. 60-78.

Kaiser et al., "Heart failure depresses endothelium-dependent responses in canine femoral artery," *Am. J. Physiol.*, 1989, 256:H962-H967.

Kandabashi et al., "Inhibition of myosin phosphatase by upregulated rho-kinase plays a key role for coronary artery spasm in a porcine model with interleukin-1$\beta$," *Circulation*, 2000, 101:1319-1323.

Karim et al., "Vascular reactivity in heart failure: role of myosin light chain phosphatase," *Circ. Res.*, 2004, 95:612-618.

Katz et al., "Impaired acetylcholine-mediated vasodilation in patients with congestive heart failure. Role of endothelium-derived vasodilating and vasoconstricting factors," *Circulation*, 1993, 88:55-61.

Khaper and Singal, "Effects of afterload-reducing drugs on pathogenesis of antioxidant changes and congestive heart failure in rats," *J. Am. Coll. Cardiol.*, 1997, 29:856-861.

Khatri et al., "Role of myosin phosphatase isoforms in cGMP-mediated smooth muscle relaxation," *J. Biol. Chem.*, 2001, 276(40):37250-37257.

Konstam, "Improving clinical outcomes with drug treatment in heart failure: what have trials taught?" *Am. J. Cardiol.*, 2003, 91(suppl):9D-14D.

Kubo et al., "Endothelium-dependent vasodilation is attenuated in patients with heart failure," *Circulation*, 1991, 84:1589-1596.

Levine et al., "Elevated circulating levels of tumor necrosis factor in severe chronic heart failure," *N. Engl. J. Med.*, 1990, 323:236-241.

Li et al., "Differential effect of hydrogen peroxide and superoxide anion on apoptosis and proliferation of vascular smooth muscle cells," *Circulation*, 1997, 96(10):3602-3609.

Lincoln et al., "Invited review: cGMP-dependent protein kinase signaling mechanisms in smooth muscle: from the regulation of tone to gene expression," *J. Appl. Physiol.*, 2001, 91:1421-1430.

Mann, "Inflammatory mediators and the failing heart: past, present, and the foreseeable future," *Circ. Res.*, 2002, 91:988-998.

Mendelsohn, "Viagra: now mending hearts," *Nature Medicine*, 2005, 11(2):115-116.

Miller et al., "Sustained reduction of cardiac impedance and preload in congestive heart failure with the antihypertensive vasodilator prazosin," *N. Engl. J. Med.*, 1977, 297:303-307.

Miguel et al., "Acute and chronic captopril, but not prazosin or nifedipine, normalize alterations in adrenergic intracellular $Ca^{2+}$ handling observed in the mesenteric arterial tree of spontaneously hypertensive rats," *J. Pharmacol. Exp. Ther.*, 2005, 313:359-367.

Morgan et al., "Validation of echocardiographic methods for assessing left ventricular dysfunction in rats with myocardial infarction," *Am. J. Physiol. Heart Circ. Physiol.*, 2004, 287:H2049-H2053.

Nickenig and Harrison, "The $AT_1$-type angiotensin receptor in oxidative stress and atherogenesis. Part II: $AT_1$ receptor regulation," *Circulation*, 2002, 105:530-536.

Nickenig and Harrison, "The $AT_1$-type angiotensin receptor in oxidative stress and atherogenesis: Part I: oxidative stress and atherogenesis," *Circulation*, 2002, 105:393-396.

Parris et al., "Tumour necrosis factor-$\alpha$ activates a calcium sensitization pathway in guinea-pig bronchial smooth muscle," *J. Physiol.*, 1999, 518:561-569.

Pfeffer et al., "Effect of captopril on mortality and morbidity in patients with left ventricular dysfunction after myocardial infarction. Results of the survival and ventricular enlargement trial," *N. Engl. J. Med.*, 1992, 327(10):669-677.

Pfeffer et al., "Hemodynamic benefits and prolonged survival with long-term captopril therapy in rats with myocardial infarction and heart failure," *Circulation*, 1987, 75(suppl I):I-149-I-155.

Pfeffer et al., "Influence of chronic captopril therapy on the infarcted left ventricle of the rat," *Circ. Res.*, 1985, 57:84-95.

Rondelet et al., "Signaling Molecules in Overcirculation-Induced Pulmonary Hypertension in Piglets—Effect of Sildenafil Therapy," *Circulation*, 2004, 110:2220-2225.

Rosen et al., "Development and evaluation of an abridged, 5-item version of the International Index of Erectile Function (IIEF-5) as a diagnostic tool for erectile dysfunction," *Intl. J. Impot. Res.*, 1999, 11:319-326.

Rosen et al., "The Female Sexual Function Index (FSFI): A Multidimensional Self-Report Instrument for the Assessment of Female Sexual Function," *J. Sex Marital Ther.*, 2000, 26:191-208.

Selye et al., "Simple techniques for the surgical occlusion of coronary vessels in the rat," *Angiology*, 1960, 11:398-407.

Somlyo and Somlyo, "$Ca^{2+}$ sensitivity of smooth muscle and nonmuscle myosin II: modulated by G proteins, kinases, and myosin phosphatase,"*Physiol. Rev.*, 2003, 83:1325-1358.

Surks et al., "Regulation of myosin phosphatase by a specific interaction with cGMP-dependent protein kinase 1$\alpha$" *Science*, 1999, 286:1583-1587.

Takimoto et al., "Chronic inhibition of cyclic GMP phosphodiesterase 5A prevents and reverses cardiac hypertrophy," *Nature Medicine*, 2005, 11(2):214-222.

Taylor et al., "Combination of isosorbide dinitrate and hydralazine in blacks with heart failure," *N. Engl. J. Med.*, 2004, 351(20):2049-2057.

Torre-Amione et al., "Proinflammatory cytokine levels in patients with depressed left ventricular ejection fraction: a report from the Studies of Left Ventricular Dysfunction (SOLVD)," *J. Am. Coll. Cardiol.*, 1996, 27:1201-1206.

Tsutamoto et al., "Interleukin-6 spillover in the peripheral circulation increases with the severity of heart failure, and the high plasma level of interleukin-6 is an important prognostic predictor in patients with congestive heart failure," *J. Am. Coll. Cardiol.*, 1998, 31:391-398.

Warnholtz et al., "Increased NADH-oxidase-mediated superoxide production in the early stages of atherosclerosis: evidence for involvement of the renin-angiotensin system," *Circulation*, 1999, 99:2027-2033.

Wooldridge et al., "Smooth muscle phosphatase is regulated in Vivo by exclusion of phosphorylation of threonine 696 of MYPT1 by phosphorylation of Serine 695 in response to cyclic nucleotides," *J. Biol. Chem.*, 2004, 279(33):34496-34504.

Yusuf et al., "Effect of enalapril on myocardial infarction and unstable angina in patients with low ejection fractions,"*Lancet*, 1992, 340:1173-1178.

Yusuf et al., "Effects of an angiotensin-converting-enzyme inhibitor, ramipril, on cardiovascular events in high-risk patients," *N. Engl. J. Med.*, 2000, 342(3):145-153.

Zafari et al., "Role of NADH/NADPH oxidase-derived $H_2O_2$ in angiotensin II-induced vascular hypertrophy," *Hypertension*, 1998, 32:488-495.

Zalba et al., "Oxidative stress in arterial hypertension: role of NAD(P)H oxidase," *Hypertension*, 2001, 38:1395-1399.

SEXUAL DYSFUNCTION

CROSS-REFERENCE TO RELATED APPLICATIONS

This application is a National Stage application under 35 U.S.C. §371 and claims benefit under 35 U.S.C. §119(a) of International Application No. PCT/US2006/047044 having an International Filing Date of Dec. 8, 2006, which claims the benefit of priority of U.S. Provisional Application Ser. No. 60/749,182, having a filing date of Dec. 9, 2005.

STATEMENT AS TO FEDERALLY SPONSORED RESEARCH

This invention was made with government support under grant numbers HL064137/HL069894 awarded by the National Heart, Lung, and Blood Institute/National Heart Lung, and Blood Institute. The government has certain rights in the invention.

BACKGROUND

1. Technical Field

This document relates to methods and materials involved in treating mammals (e.g., humans) having a sexual dysfunction that is refractory to treatment with a phosphodiesterase V (PDE V) inhibitor. For example, this document relates to methods and compositions for treating a sexual dysfunction (e.g., erectile dysfunction) refractory to PDE V inhibition using an angiotensin-converting enzyme (ACE) inhibitor and/or an angiotensin II receptor blocker and a PDE V inhibitor.

2. Background Information

Nitric oxide (NO) is a lipophilic, free radical gas that has many physiological functions, such as mediating vasodilation. The endothelial isoform of nitric oxide synthase is a key source of NO in the cardiovascular system. NO that is generated by endothelial cells diffuses into adjacent smooth muscle cells where it binds to a heme moiety on guanylyl cyclase and activates the enzyme to produce cGMP from GTP. Increased cGMP activates cGMP-dependent protein kinase type Iα (PKGIα). One of the targets of PKGIα in smooth muscle is myosin light chain (MLC) phosphatase. Activation of MLC phosphatase leads to dephosphorylation of myosin light chains, thereby decreasing smooth muscle tension and causing vasodilation.

MLC phosphatase is a holoenzyme consisting of a catalytic subunit (PP1cδ), a myosin-targeting subunit (MYPT1), and a 20-kDa subunit of unknown function. The MYPT1 subunit has four major isoforms, which are produced by alternative RNA splicing of two different exons. Tissue-specific and developmentally regulated alternative splicing of a 123-bp central exon produces a 41-amino acid central insert. Alternative splicing of the 31-bp 3'-exon is responsible for expression of leucine zipper positive (LZ⁻) or leucine zipper negative (LZ⁻) MYPT1 isoforms. Specifically, exclusion of the 3'-exon shifts the reading frame of the MYPT1 transcript to encode a carboxy terminal LZ domain. The carboxy terminal LZ domain of the MYPT1 subunit is required for activation of MLC phosphatase by PKGIα.

SUMMARY

This document provides methods and materials related to treating mammals with a sexual dysfunction that is refractory to treatment with a PDE V inhibitor. For example, this document provides methods and materials for using an ACE inhibitor and/or an angiotensin II receptor blocker with a PDE V inhibitor to treat mammals having a sexual dysfunction (e.g., erective dysfunction) that is unresponsive to treatment with a PDE V inhibitor alone. Treating problems with sexual function can improve quality of life.

While not being limited to any particular mode of action, PDE V inhibitors can prevent the breakdown of cGMP in the corpus cavernosum smooth muscle, which can lead to vessel dilation and erection. A large percentage of men do not respond to PDE V inhibition for the treatment of erectile dysfunction. Unresponsiveness to PDE V inhibition can be due to downregulated expression of the LZ+ isoform of the MYPT1 subunit of MLC phosphatase in the corpus cavernosum. PKGIα, which is activated by cGMP, cannot activate MLC phosphatase with a LZ⁻ MYPT1 subunit. In spite of PDE V inhibition resulting in an increase in cGMP in the penile smooth muscle, downregulated LZ⁺ MYPT1 isoform expression can result in unresponsiveness to this class of therapeutics.

This document is based, in part, on the discovery that ACE inhibitors can maintain endogenous levels of expression of the LZ⁺ MYPT1 isoform and can increase sensitivity to cGMP-mediated vasodilation. As described herein, an ACE inhibitor and/or an angiotensin II receptor blocker can be used with a PDE V inhibitor to treat a mammal (e.g., a human) having a sexual dysfunction (e.g., erectile dysfunction) that is refractory to treatment with a PDE V inhibitor alone.

In general, one aspect of this document features a method for increasing a mammal's responsiveness to treatment of a sexual dysfunction with a PDE V inhibitor. The method comprises, or consists essentially of, administering, to a mammal having a sexual dysfunction, a PDE V inhibitor and an agent selected from the group consisting of ACE inhibitors and angiotensin II receptor blockers under conditions wherein the mammal's sexual function improves to a level greater than the level when the mammal is treated with the PDE V inhibitor in the absence of the agent. The mammal can be a human (e.g., a human male). The sexual dysfunction can be an erectile dysfunction. The agent can be an ACE inhibitor selected from the group consisting of captopril and ramipril. The agent can be an angiotensin II receptor blocker selected from the group consisting of losartan, valsartan, irbesartan, and candesartan. The PDE V inhibitor can be selected from the group consisting of sildenafil, tadalafil, and vardenafil. The agent can be administered before the PDE V inhibitor. The agent can be administered at the same time as the PDE V inhibitor. The agent can be administered after the PDE V inhibitor. The method can comprise administering an ACE inhibitor and an angiotensin II receptor blocker.

In another aspect, this document features a composition comprising, or consisting essentially of, a PDE V inhibitor and an agent selected from the group consisting of ACE inhibitors and angiotensin II receptor blockers. The PDE V inhibitor can be selected from the group consisting of sildenafil, tadalafil, and vardenafil. The agent can be an angiotensin II receptor blocker selected from the group consisting of losartan, valsartan, irbesartan, and candesartan. The agent can be an ACE inhibitor selected from the group consisting of captopril and ramipril. The composition, upon administration to a mammal, can release the agent before releasing the PDE V inhibitor. The composition, upon administration to a mammal, can provide sustained release of the agent and a burst of release of the PDE V inhibitor. The composition can comprise the PDE V inhibitor encapsulated within a solid dosage form comprising the agent. The composition can comprise the PDE V inhibitor, an ACE inhibitor, and an angiotensin II receptor blocker.

In another aspect, this document features a composition comprising, or consisting essentially of, sildenafil, tadalafil, or vardenafil in combination with captopril, ramipril, losartan, valsartan, irbesartan, or candesartan.

In another aspect, this document features the use of a PDE V inhibitor and an agent selected from the group consisting of ACE inhibitors and angiotensin II receptor blockers in the manufacture of a medicament for treating sexual dysfunction. The PDE V inhibitor can be selected from the group consisting of sildenafil, tadalafil, and vardenafil. The agent can be an angiotensin II receptor blocker selected from the group consisting of losartan, valsartan, irbesartan, and candesartan. The agent can be an ACE inhibitor selected from the group consisting of captopril and ramipril.

In another aspect, this document features the use of a PDE V inhibitor and an agent selected from the group consisting of ACE inhibitors and angiotensin II receptor blockers in the manufacture of a medicament for treating sexual dysfunction that is unresponsive to treatment with a PDE V inhibitor alone. The PDE V inhibitor can be selected from the group consisting of sildenafil, tadalafil, and vardenafil. The agent can be an angiotensin II receptor blocker selected from the group consisting of losartan, valsartan, irbesartan, and candesartan. The agent can be an ACE inhibitor selected from the group consisting of captopril and ramipril.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
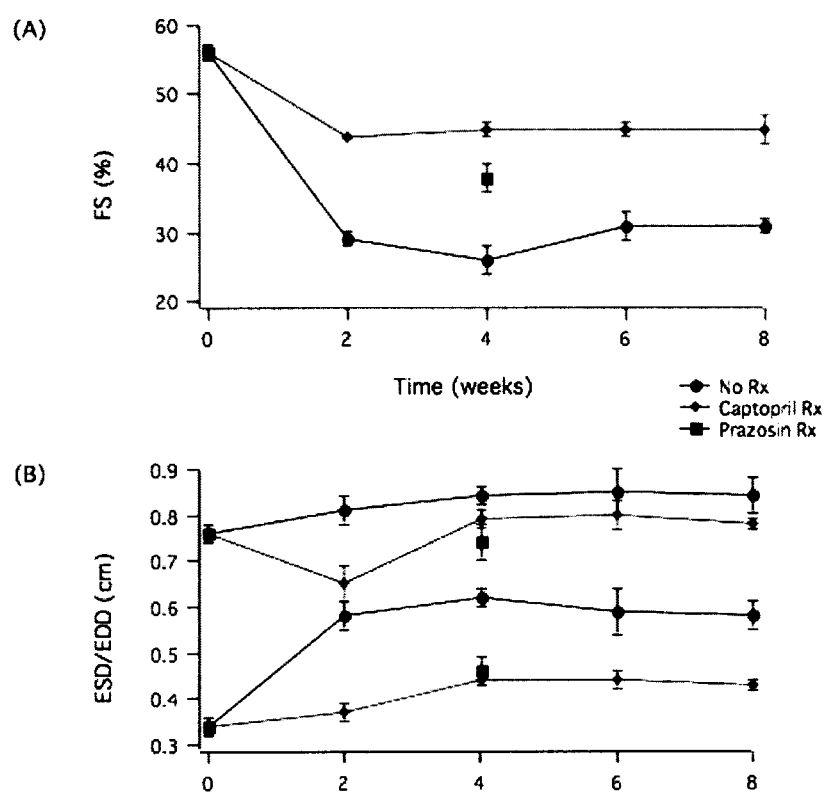
FIG. 1A is a graph plotting fractional shortening (FS=((EDD−ESD)/EDD)×100%) versus time (weeks) after left anterior descending coronary artery (LAD) ligation.
FIG. 1B is a graph plotting end systolic dimension (ESD) and end diastolic dimension (EDD) versus time (weeks) after LAD ligation. Data points are mean±SEM for n=4 to 5 in congestive heart failure (CHF) without treatment (●), CHF treated with captopril (♦), and CHF treated with prazosin (■), respectively.

This document provides methods and materials related to treating mammals (e.g., humans) having a sexual dysfunction unresponsive to treatment with a PDE V inhibitor. For example, this document provides methods and materials for using an ACE inhibitor and/or an angiotensin II receptor blocker with a PDE V inhibitor to treat human males having erectile dysfunction refractory to treatment with a PDE V inhibitor (e.g., Viagra) alone.

Any mammal can be treated for a sexual dysfunction refractory to PDE V inhibition. For example, a male or female human, horse, or cow can be treated for a sexual dysfunction. In addition, the mammal (e.g., human) can have a vascular condition, such as hypertension, diabetes, or congestive heart failure.

Any sexual dysfunction refractory to treatment with a PDE V inhibitor can be treated using an ACE inhibitor and a PDE V inhibitor, or using an angiotensin II receptor blocker and a PDE V inhibitor, or using an ACE inhibitor, an angiotensin II receptor blocker, and a PDE V inhibitor. For example, male dysfunctions, such as erectile dysfunction, priapism, and premature ejaculation, that are refractory to treatment with a PDE V inhibitor can be treated. In addition, female dysfunctions, such as female sexual arousal disorders, decreased vaginal engorgement, and vaginismus, that are refractory to treatment with a PDE V inhibitor can be treated.

Any method can be used to identify a mammal (e.g., a human) having a sexual dysfunction. For example, a physical exam can be performed to identify a mammal having a sexual dysfunction. A medical and sexual history also can be used to identify a mammal (e.g., a human) having a sexual dysfunction. In addition, a scale, such as the International Index of Erectile Function (IIEF; Rosen et al., *Intl. J. Impot. Res.*, 11:319-326 (1999)) or the Female Sexual Function Index (FSFI; Rosen, *J. Sex Marital Ther,* 26:191-208 (2000)), can be used to identify humans having a sexual dysfunction. For example, a human male can be identified as having erectile dysfunction if he has a score of 21 or less on the IIEF, whereas a score of 23 or higher on the IIEF indicates that a human male does not have erectile dysfunction. A sexual dysfunction can also be identified by performing a test, such as a genital blood flow test that uses duplex Doppler ultrasonography to determine peak systolic and diastolic velocities of blood flow to the clitoris, labia, urethra, and vagina.

Once a mammal is identified as having a sexual dysfunction, it can be determined whether or not the sexual dysfunction is refractory to treatment with a PDE V inhibitor. A PDE V inhibitor, such as sildenafil, vardenafil, or tadalafil, can be administered to a mammal before intercourse (e.g., one, two, six, eight, or 12 hours before intercourse, depending on the agent administered). The responsiveness of a sexual dysfunction to treatment with a PDE V inhibitor can be assessed following sexual stimulation. Any method can be used to determine whether a sexual dysfunction is refractory or responsive to treatment with a PDE V inhibitor. For example, an IIEF or FSFI score can be determined before and after treatment with a PDE V inhibitor and compared to assess responsiveness of a sexual dysfunction to treatment with a PDE V inhibitor. In some cases, the absence of a change in the IIEF score or the FSFI score indicates that a sexual dysfunction is unresponsive to treatment with a PDE V inhibitor. In some cases, information from a patient can be used to determine whether or not a sexual dysfunction is refractory to treatment with a PDE V inhibitor. The sexual function of a mammal also can be assessed after a PDE V inhibitor is administered multiple times over a period of time, such as two times per week for a month, and compared to the sexual function assessed prior to treatment to determine whether or not the sexual function improves.

A mammal identified as having a sexual dysfunction that is refractory to treatment with a PDE V inhibitor can be treated using an ACE inhibitor and/or an angiotensin II receptor blocker with a PDE V inhibitor. Any ACE inhibitor, such as captopril (Capoten®), benazepril (Lotensin®), enalapril (Vasotec®), lisinopril (Prinivil®, Zestril®) fosinopril (Monopril®), ramipril (Altace), perindopril (Aceon®), quinapril (Accupril®), moexipril (Univasc®), or trandolapril (Mavik®), and any PDE V inhibitor, such as vardenafil (Levitra®, Nuviva®), tadalafil (Clalis®), zaprinast, sildenafil (Viagra®), or dipyridamole (Persantine), can be used to treat a sexual dysfunction that is unresponsive to treatment with a PDE V inhibitor alone. In addition, any angiotensin II receptor blocker, such as losartan (Cozaar®), valsartan (Diovan®), irbesartan (Avapro®), or candesartan (Atacand®) can be used to treat a sexual dysfunction that is unresponsive to treatment with a PDE V inhibitor. A sexual dysfunction refractory to PDE V inhibition also can be treated using one or more ACE inhibitors and one or more PDE V inhibitors, or using one or more angiotensin II receptor blockers and one or more PDE V inhibitors, or using one or more ACE inhibitors, one or more angiotensin II receptor blockers, and one or more PDE V inhibitors. More than one agent of a therapeutic class can be used concomitantly or in succession. A sexual dysfunction that is refractory to treatment with a PDE V inhibitor can be treated without using an endothelin antagonist or a sex hormone.

A PDE V inhibitor and an ACE inhibitor and/or an angiotensin II receptor blocker can be administered to a mammal in any order. For example, an ACE inhibitor and/or an angiotensin II receptor blocker can be administered first to a mammal, followed by administration of a PDE V inhibitor. Alternatively, a PDE V inhibitor can be administered first, followed by administration of an ACE inhibitor and/or an angiotensin II receptor blocker.

A PDE V inhibitor and an ACE inhibitor and/or an angiotensin II receptor blocker can be administered to a mammal in any amount, at any frequency, and for any duration effective to achieve a desired outcome (e.g., to relieve a symptom of a sexual dysfunction or improve sexual function) without producing significant toxicity to the mammal. In some cases, a PDE V inhibitor and an ACE inhibitor and/or an angiotensin II receptor blocker can be administered to a mammal to improve sexual function by 5, 10, 25, 50, 75, 99, or more percent. Any method can be used to determine whether or not sexual function improves. For example, sexual dysfunction scores, such as IIEF scores or FSFI scores, can be determined at different time points and compared to evaluate whether or not sexual function improves. In some cases, the sexual dysfunction score can be determined prior to treatment and compared to the sexual dysfunction score determined during or after treatment to establish whether or not sexual function improved. In some cases, information from a patient can be used to determine whether or not sexual function improved.

Effective amounts of therapeutic agents will depend on various factors, such as the activities of the particular agents used, the frequency of administration, the duration of treatment, the severity of the sexual dysfunction being treated, and the condition and prior medical history of the mammal being treated. In some cases, a commonly prescribed amount of an ACE inhibitor, an angiotensin II receptor blocker, or a PDE V inhibitor can be used. For example, the dose of sildenafil can be 50 mg or 100 mg, the dose of vardenafil can be 10 mg or 20 mg, the dose of losartan can be 25 to 100 mg, and the dose of captopril can be 6.25 to 50 mg. In some cases, a commonly prescribed amount can be used to estimate an effective dose. A dose that is lower than an effective dose can initially be administered to a mammal, and the dose can then be gradually increased over time until the desired effect is achieved.

The frequency and duration of administration can be any frequency or duration that improves sexual function without being toxic. For example, an ACE inhibitor or an angiotensin II receptor blocker can be administered once or twice a day. A PDE V inhibitor can be administered once, twice, or three times a week, or as needed. The frequency of administration can remain constant or can be variable during the duration of treatment. An effective duration of treatment can vary from several weeks to several months or years. For example, an effective duration of treatment can be six months, four years, or a lifetime. In addition, a course of treatment can include rest periods. Multiple factors can influence the actual effective frequency and duration of treatment. For example, the activities of the particular therapeutic agents used, the severity of the sexual dysfunction being treated, the doses administered, and the condition and prior medical history of the mammal being treated can affect the effective frequency and duration of treatment.

This document also provides compositions including one or more ACE inhibitors and one or more PDE V inhibitors, compositions including one or more angiotensin II receptor blockers and one or more PDE V inhibitors, as well as compositions including one or more ACE inhibitors, one or more angiotensin II receptor blockers, and one or more PDE V inhibitors. Such compositions can be used as described herein to treat mammals having sexual dysfunctions refractory to treatment with a PDE V inhibitor. In some cases, compositions including one or more of an ACE inhibitor, an angiotensin II receptor blocker, and a PDE V inhibitor in an amount that is lower than that used to treat hypertension or sexual dysfunction can be used. Compositions can be formulated for any route of administration, e.g., oral or topic administration, and can include one or more pharmaceutically acceptable excipients. Solid dosage forms for oral administration include capsules, tablets, pills, and powders. Solid dosage forms can include one or more therapeutic agents with at least one excipient or carrier, such as a buffering agent, an absorption accelerator, a coating, or a disintegrating agent. In addition, a composition can be formulated for delayed release, controlled release, sustained release, or extended release. Compositions including more than one, e.g., two, active ingredients can be formulated such that the release profile of each active ingredient differs. For example, a composition can be formulated such that an ACE inhibitor or angiotensin II receptor blocker is released first, followed by release of a PDE V inhibitor. In some cases, an ACE inhibitor or angiotensin II receptor blocker can have a sustained release, followed by a burst of PDE V inhibitor. Such a formulation can, for example, include a PDE V inhibitor that is encapsulated within a solid dosage form comprising an ACE inhibitor or an angiotensin II receptor blocker.

The invention will be further described in the following examples, which do not limit the scope of the invention described in the claims.

EXAMPLES

Example 1

Maintaining LZ+ MYPT1 Isoform Expression by ACE Inhibition

A surgical infarct model of CHF (Delp et al., *J. Appl. Physiol.*, 83:1291-99 (1997); Selye et al., *Angiology*, 11:398-407 (1960)), was used with a protocol approved by the Institutional Animal Care and Use Committee of Case Western Reserve University. Adult male Sprague-Dawley rats (Harlan, Indianapolis, Ind.) weighing 400-450 grams were put under general anesthesia by intraperitoneal injection with a mixture (3:3:2) of ketamine (100 mg/mL), xylazine (20 mg/mL), and acepromazine (10 mg/mL). After intubation, the rats were ventilated continuously (room air) using a small animal ventilator (model 683, Harvard Apparatus, Holliston, Mass.). A left lateral thoracotomy incision was made along the 5th intercostal space. After the pericardium was opened, the heart was exteriorized using a retention suture placed at the apex. The left anterior descending coronary artery (LAD) was ligated twice using 6-0 prolene suture (Ethicon, Piscataway, N.J.). After chest closure with running 3-0 vicryl suture (Ethicon), rats were placed in a recovery chamber with a heating pad and a warming light. The post-operative survival rate of 60-70% was consistent with other studies (Delp et al., *J. Appl. Physiol.*, 83:1291-99 (1997)).

Beginning on post-operative day one, rats were allowed to drink ad libitum. One group was fed water with captopril (2 g/L), and another group was fed water alone (Pfeffer et al., *Circ. Res.*, 57:84-95 (1985)). The rats were fed a standard diet of Teklad rodent feed (Harlan) ad libitum and kept on a 12:12 hour light-dark cycle. In both the captopril- and the placebo-treated group, the rats were sacrificed at designated time intervals of 2 weeks and then 4, 6, and 8 weeks after surgery. On average, the rats drank approximately 20 mL of water daily, which corresponded to a dose of 100 mg/kg/day of captopril. A third group of rats was given prazosin (2 mg/kg/day) for 4 weeks before being sacrificed (Miguel et al., *J. Pharmacol. Exp. Ther.*, 313:359-67 (2005)).

All rats in the placebo- and captopril-treated groups underwent transthoracic echocardiography (Acuson Sequoia C256® Echocardiography System, Siemens Medical Solutions USA, Inc., Malvern, Pa.) at baseline prior to LAD ligation and at 2, 4, 6, and 8 weeks after LAD ligation using 2-D digital loop imaging under conscious sedation with vaporized isoflurane as described previously (Karim et al., *Circ. Res.*, 95:612-18 (2004); Morgan et al., *Am. J. Physiol. Heart Circ. Physiol.*, 287:H2049-H2053 (2004)). Rats in the prazosin-treated group also underwent transthoracic echo prior to being sacrificed at 4 weeks after infarction. Both parasternal long and short axis views were obtained using a 13-MHz linear array transducer. Digital calipers were used to measure end systolic dimension (ESD) and end diastolic dimension (EDD). Cardiac function was estimated using fractional shortening (FS) obtained from the EDD and ESD in the parasternal long axis view and calculated as FS=((EDD−ESD)/EDD)×100%.

The echocardiographic data were reported as mean±SEM. There were two groups (infarct only versus infarct+captopril, n=4-5 rats) at each time point, except at the 4 week time point when a third group of infarct rats was treated with prazosin (n=5). The difference between the means was determined using an ANOVA and Tukey's Honestly Significantly Different Test, and P<0.05 was reported as significant.

Transthoracic echocardiography of uninfarcted rats demonstrated normal cardiac function with FS of 56±1%. After LAD ligation, FS significantly decreased to 29±1% at 2 weeks post-infarction (P<0.05) and remained depressed at 4, 6, and 8 weeks post-surgery (FIG. 1A, P<0.05). The fall in FS was due to an increase in ESD after the myocardial infarction (P<0.05) rather than a change in EDD (FIG. 1B). EDD tended to increase following the LAD ligation but did not reach statistical significance (P>0.05). Treatment with captopril reduced the ESD compared to placebo at all time-points (P<0.05). Overall, captopril attenuated the fall in FS and improved left ventricular function (LVF) as early as 2 weeks post-infarction. Comparing the captopril versus prazosin treated group at 4 weeks after surgery indicated that prazosin was as effective as captopril in restoring LVF (FS 38±2% vs. 45±1%, P=0.11). This suggested that prazosin improved fractional shortening compared to placebo (P<0.05) via its documented afterload reducing effect (Awan et al., *Circulation*, 56:346-54 (1977); Miller et al., *N Engl. J. Med.*, 297: 303-07 (1977)).

MYPT1 isoform expression was analyzed in uninfarcted control animals prior to LAD ligation and in rats at 2, 4, 6, and 8 weeks after LAD ligation using Western blotting. Western blotting was performed as described previously (Karim et al., *Circ. Res.*, 95:612-18 (2004); Huang et al., *J. Biol. Chem.*, 279:597-603 (2004)), and the blots were normalized for protein loading. Briefly, total protein was extracted after tissues of aorta, iliac artery, and portal vein were frozen with liquid nitrogen, pulverized into fine powder, and resuspended in SDS sample buffer. MYPT1 polypeptides were resolved by SDS-polyacrylamide gel electrophoresis (SDS-PAGE) using 6% gels with an acrylamide/bisacrylamide ratio of 29:1. Following SDS-PAGE separation, protein bands were electrophoretically transferred onto a nitrocellulose membrane (NitroBind, cast, pure nitrocellulose 0.22 micron, Osmonics, Minnetonka, Minn.) in buffer containing 25 mmol/L Tris-HCl, 192 mmol/L glycine, and 10% methanol (v/v). The membranes were subsequently blocked in 1×TBS with 3% milk and 0.05% TWEEN for 1 hour and incubated with a polyclonal anti-MYPT1 antibody (Covance F38.130, PRB-457C) and a monoclonal anti-LZ+MYPT1 isoform antibody (Karim et al., *Circ. Res.*, 95:612-18 (2004)). Secondary antibodies specific to the primary antibodies were conjugated to HRP for enhanced chemiluminance (ECL). The protein bands were visualized on the blot using an ECL Plus Western Blot detection system (Amersham Biosciences, Piscataway, N.J.). The blots were scanned using densitometry and the intensities of the bands were analyzed. All band intensities were in the linear range of the detection system.

The Western blot data were reported as mean±SEM. There were two groups (infarct only versus infarct+captopril, n=4-5 rats) at each time point, except at the 4 week time point when a third group of infarct rats was treated with prazosin (n=5). The difference between the means was determined using an ANOVA and Tukey's Honestly Significantly Different Test, and P<0.05 was reported as significant.

Figure 2:
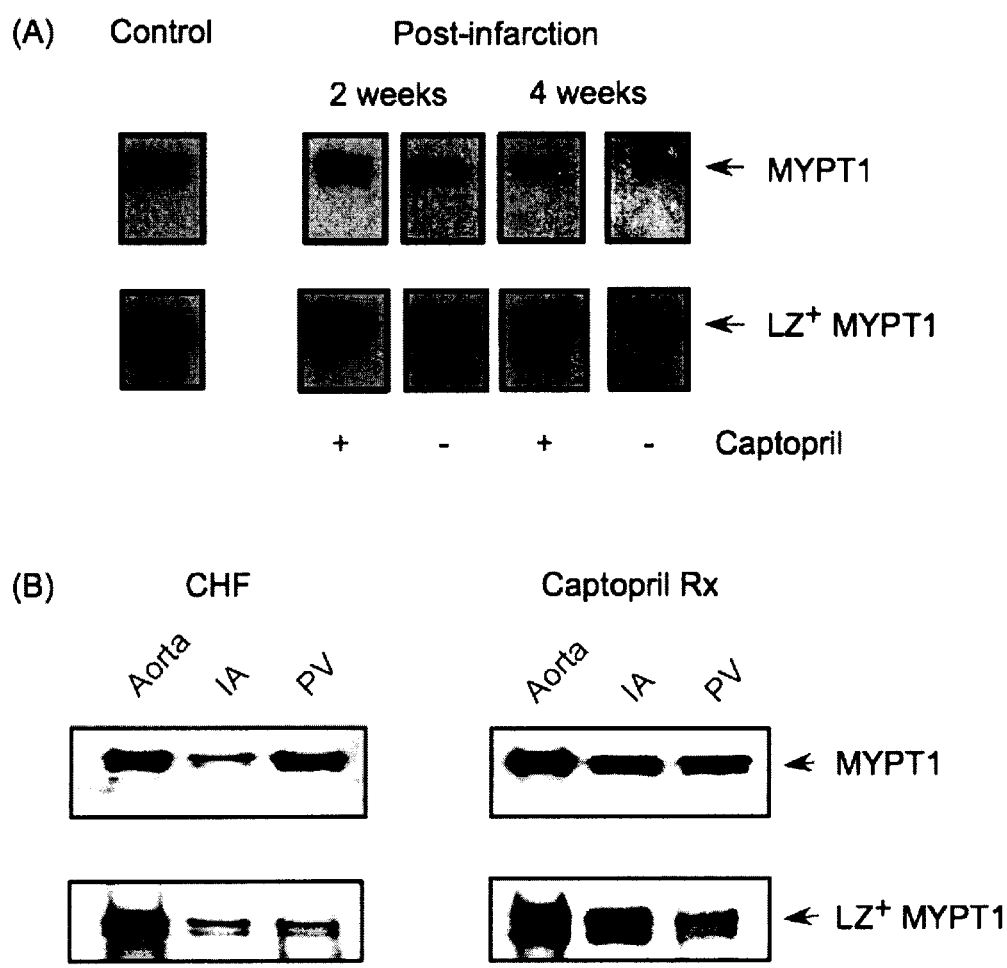
FIG. 2A contains Western blots analyzing the iliac artery of uninfarcted control (Control) rats and infarct rats at 2 and 4 weeks after LAD ligation. The blots were probed using an antibody directed against MYPT1 polypeptide (top panels) and a monoclonal antibody specific for the LZ$^+$ MYPT1 isoform (bottom panels).
FIG. 2B contains Western blots analyzing the aorta, iliac artery, and portal vein smooth muscles at 8 weeks following LAD ligation of untreated (left three lanes) and captopril-treated (right three lanes) rats with CHF using an antibody directed against MYPT1 polypeptide (top panels) and a monoclonal antibody specific for the LZ$^+$ MYPT1 isoform (bottom panels).
Figure 3:
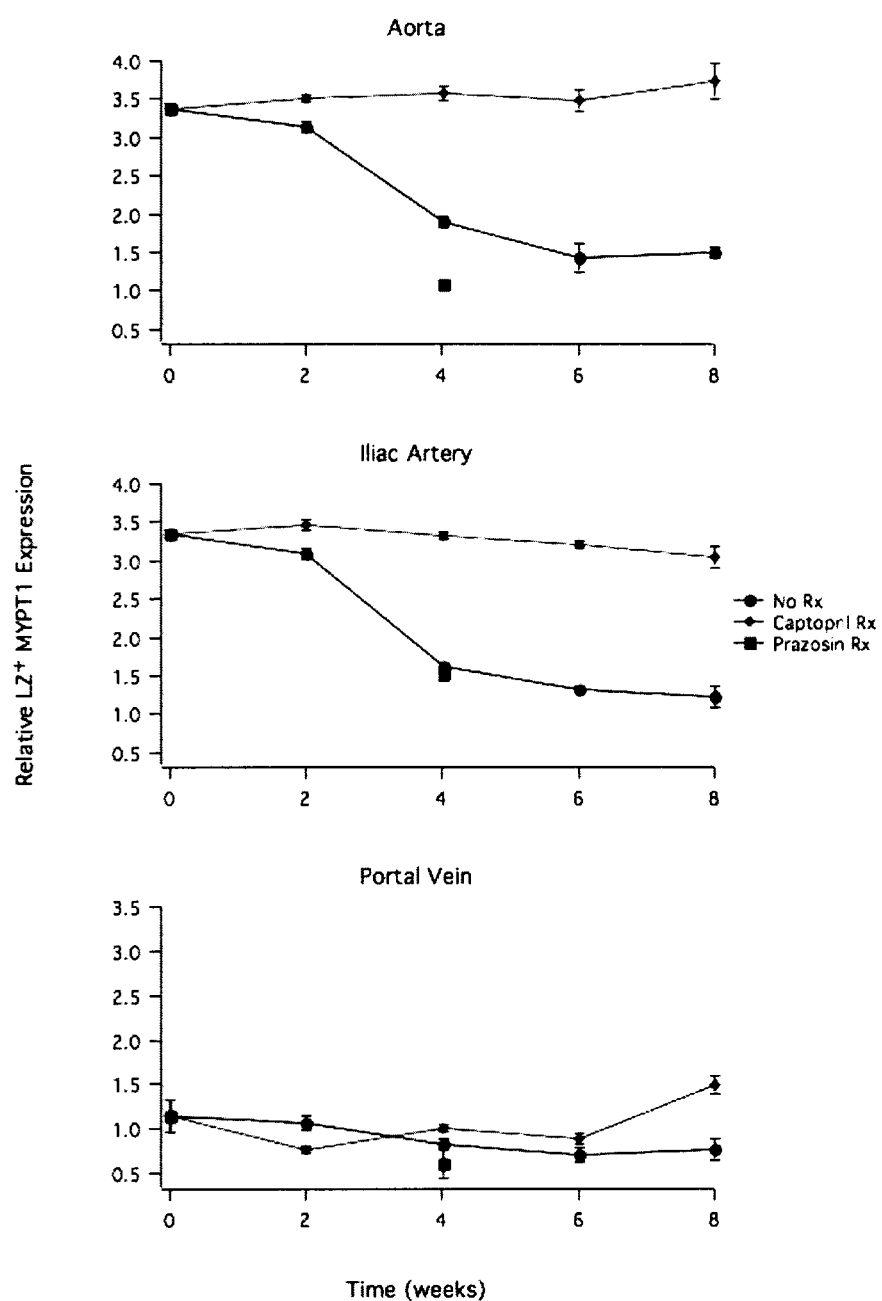
FIG. 3 contains graphs plotting relative LZ$^+$ MYPT1 isoform expression versus time (weeks) after LAD ligation in the aorta (top graph), iliac artery (middle graph), and portal vein (bottom graph). Data points are mean±SEM for n=4 to 5 at each time point in CHF without treatment (●), CHF with captopril (♦), and CHF with prazosin (■).

Western Blot analysis of MYPT1 isoform expression in uninfarcted control animals prior to LAD ligation and in rats at 2, 4, 6, and 8 weeks after LAD ligation was performed using a polyclonal MYPT1 antibody and a monoclonal antibody specific for the LZ+MYPT1 isoform (Karim et al., *Circ. Res.*, 95:612-18 (2004)). These antibodies have different affinities for MYPT1 polypeptide, but the relative expression of the LZ+MYPT1 isoform can be determined by calculating the ratio of the density of the LZ+MYPT1 isoform band to the total MYPT1 polypeptide band (FIGS. 2 and 3).

Consistent with prior data (Karim et al., *Circ. Res.*, 95: 612-18 (2004)), $LZ^+$ MYPT1 isoform expression predominated in uninfarcted iliac artery (IA) smooth muscle (FIG. 2A). At two weeks post-infarction, there was a small decrease in the relative $LZ^+$ MYPT1 isoform expression in untreated IA (7.8±0.1%, P<0.033, FIG. 2A) and $LZ^+$ MYPT1 isoform expression fell further at 4 weeks post LAD ligation (52±2%, P<0.05, FIG. 2A). In untreated animals, $LZ^+$ MYPT1 isoform expression in the IA remained at this lower level at both 6 and 8 weeks post MI (FIGS. 2B and 3). In captopril treated animals, MYPT1 polypeptide expression in the IA was preserved at the level of the uninfarcted control smooth muscle (P>0.05, FIGS. 2 and 3).

In rat aorta (Ao), similar to the IA and prior studies (Karim et al., *Circ. Res.*, 95:612-18 (2004)), $LZ^+$ MYPT1 isoform expression predominated in the uninfarcted tissue (FIG. 3). Following LAD ligation in the untreated animals, there was a small decrease in $LZ^+$ MYPT1 isoform expression at 2 weeks (7.1±0.2%, P=0.033, FIG. 3), and $LZ^+$ MYPT1 isoform expression fell further between 2-4 weeks post-infarction (44±1%, P<0.05, FIG. 3). The relative expression of the $LZ^+$ MYPT1 isoform in the aorta then remained at this lower level at both 6 and 8 weeks following the MI (FIGS. 2B and 3). In the animals treated with captopril, $LZ^+$ MYPT1 isoform expression in the aorta was preserved at the uninfarcted control level (P>0.05, FIG. 3).

In the portal vein (PV), $LZ^+$ MYPT1 isoform expression in uninfarcted control smooth muscle was much lower than that in the Ao and IA (Karim et al., *Circ. Res.*, 95:612-18 (2004)) and remained low in both placebo and captopril treated groups at all time intervals (FIGS. 2B and 3).

Since $LZ^+$ MYPT1 isoform expression fell most dramatically between 2 to 4 weeks following the myocardial infarction (MI) in untreated rats, prazosin was used to decrease afterload to determine whether blood pressure reduction alone (Awan et al., Circulation, 56:346-54 (1977); Miller et al., *N Engl. J. Med.*, 297:303-07 (1977)) via a mechanism other than renin-angiotensin blockade would have a similar effect in preserving $LZ^+$ MYPT1 isoform expression in heart failure. In contrast to the captopril-treated group, prazosin did not prevent the fall in $LZ^+$ MYPT1 isoform expression seen in the aorta or the iliac artery. In fact, $LZ^+$ MYPT1 isoform expression was lower in the aorta of the prazosin treated rats 4 weeks after infarction (68±1% vs. 44±1%, P<0.05) and was not different in the iliac artery (54±2% vs. 52±2%, P=0.87) when compared to placebo (FIG. 3).

These results indicate that ACE inhibition maintains expression of the $LZ^+$ MYPT1 isoform, which preserves sensitivity of the vasculature to nitric oxide, and that maintaining or increasing the expression of the $LZ^+$ MYPT1 isoform can be used in the treatment of CHF, hypertension, erectile dysfunction, and the invasion and metastasis of neoplasms.

Example 2

Using ACE Inhibition to Overcome Unresponsiveness to PDE V Inhibition

Ten male patients with erectile dysfunction and hypertension are enrolled in a clinical trial. The patients are not responsive to Viagra (sildenafil citrate) for the treatment of erectile dysfunction. In addition, the regimen for treatment of hypertension in the patients does not include an ACE inhibitor. The patients are switched from their current hypertension treatment to ramipril (10 mg qd) or captopril (25 mg TID). The patients are then treated with Viagra (100 mg), and their erectile function is assessed. The patients are returned to their former antihypertensive regimens that did not include an ACE inhibitor. The response to Viagra (100 mg) is determined by assessing erectile function.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing a mammal's responsiveness to treatment of a sexual dysfunction with a PDE V inhibitor, said method comprising administering, to a mammal having a sexual dysfunction, a PDE V inhibitor and an agent selected from the group consisting of ACE inhibitors and angiotensin II receptor blockers under conditions wherein the mammal's sexual function improves to a level greater than the level when said mammal is treated with said PDE V inhibitor in the absence of said agent.

2. The method of claim 1, wherein said mammal is a human.

3. The method of claim 1, wherein said mammal is a human male.

4. The method of claim 1, wherein said sexual dysfunction is erectile dysfunction.

5. The method of claim 1, wherein said agent is an ACE inhibitor selected from the group consisting of captopril and ramipril.

6. The method of claim 1, wherein said agent is an angiotensin II receptor blocker selected from the group consisting of losartan, valsartan, irbesartan, and candesartan.

7. The method of claim 1, wherein said PDE V inhibitor is selected from the group consisting of sildenafil, tadalafil, and vardenafil.

8. The method of claim 1, wherein said agent is administered before said PDE V inhibitor.

9. The method of claim 1, wherein said agent is administered at the same time as said PDE V inhibitor.

10. The method of claim 1, wherein said agent is administered after said PDE V inhibitor.

11. The method of claim 1, wherein said method comprises administering an ACE inhibitor and an angiotensin II receptor blocker.

12. A composition comprising a PDE V inhibitor and an agent selected from the group consisting of ACE inhibitors and angiotensin II receptor blockers.

13. The composition of claim 12, wherein said PDE V inhibitor is selected from the group consisting of sildenafil, tadalafil, and vardenafil.

14. The composition of claim 12, wherein said agent is an angiotensin II receptor blocker selected from the group consisting of losartan, valsartan, irbesartan, and candesartan.

15. The composition of claim 12, wherein said agent is an ACE inhibitor selected from the group consisting of captopril and ramipril.

16. The composition of claim 12, wherein said composition, upon administration to a mammal, releases said agent before releasing said PDE V inhibitor.

17. The composition of claim 12, wherein said composition, upon administration to a mammal, provides sustained release of said agent and a burst of release of said PDE V inhibitor.

18. The composition of claim 12, wherein said composition comprises said PDE V inhibitor encapsulated within a solid dosage form comprising said agent.

19. The composition of claim 12, wherein said composition comprises said PDE V inhibitor, an ACE inhibitor, and an angiotensin II receptor blocker.

20. A composition comprising sildenafil, tadalafil, or vardenafil in combination with captopril, ramipril, losartan, valsartan, irbesartan, or candesartan.

21. The composition of claim 20, wherein said composition comprises sildenafil.

22. The composition of claim 20, wherein said composition comprises tadalafil.

23. The composition of claim 20, wherein said composition comprises vardenafil.

24. The composition of claim 20, wherein said composition comprises captopril.

25. The composition of claim 20, wherein said composition comprises ramipril.

26. The composition of claim 20, wherein said composition comprises losartan.

27. The composition of claim 20, wherein said composition comprises valsartan.

28. The composition of claim 20, wherein said composition comprises irbesartan.

29. The composition of claim 20, wherein said composition comprises candesartan.

* * * * *